(12) United States Patent
Madore

(10) Patent No.: US 8,235,906 B2
(45) Date of Patent: Aug. 7, 2012

(54) SYSTEM AND METHOD FOR ACCELERATED FOCUSED ULTRASOUND IMAGING

(75) Inventor: Bruno Madore, Brookline, MA (US)

(73) Assignee: The Brigham And Women's Hospital, Inc., Boston, MA (US)

( * ) Notice: Subject to any disclaimer, the term of this patent is extended or adjusted under 35 U.S.C. 154(b) by 104 days.

(21) Appl. No.: 12/808,590

(22) PCT Filed: Dec. 30, 2008

(86) PCT No.: PCT/US2008/088518
§ 371 (c)(1), (2), (4) Date: Jun. 16, 2010

(87) PCT Pub. No.: WO2009/088845
PCT Pub. Date: Jul. 16, 2009

(65) Prior Publication Data
US 2010/0280381 A1  Nov. 4, 2010

Related U.S. Application Data

(60) Provisional application No. 61/009,683, filed on Dec. 31, 2007.

(51) Int. Cl.
*A61B 8/00* (2006.01)
(52) U.S. Cl. .................. 600/443; 600/437; 382/128
(58) Field of Classification Search .......... 600/437–466; 382/128–132
See application file for complete search history.

(56) References Cited

U.S. PATENT DOCUMENTS

| | | | |
|---|---|---|---|
| 6,351,660 B1* | 2/2002 | Burke et al. ................ 600/425 |
| 6,909,792 B1* | 6/2005 | Carrott et al. ............... 382/128 |
| 7,037,263 B2* | 5/2006 | Sumanaweera et al. ...... 600/443 |
| 7,063,666 B2* | 6/2006 | Weng et al. .................. 600/439 |
| 7,066,886 B2* | 6/2006 | Song et al. ................... 600/443 |
| 7,285,094 B2* | 10/2007 | Nohara et al. ................ 600/447 |
| 7,840,247 B2* | 11/2010 | Liew et al. ................... 600/407 |
| 7,965,761 B2* | 6/2011 | Shattil ......................... 375/147 |
| 8,002,705 B1* | 8/2011 | Napolitano et al. .......... 600/437 |
| 2003/0163046 A1* | 8/2003 | Nohara et al. ................ 600/443 |
| 2005/0043619 A1* | 2/2005 | Sumanaweera et al. ...... 600/437 |
| 2005/0288588 A1* | 12/2005 | Weber et al. ................. 600/447 |
| 2009/0030324 A1* | 1/2009 | Kato et al. .................... 600/459 |
| 2009/0110033 A1* | 4/2009 | Shattil ......................... 375/141 |
| 2010/0016725 A1* | 1/2010 | Thiele ......................... 600/447 |
| 2011/0105885 A1* | 5/2011 | Liew et al. ................... 600/410 |

OTHER PUBLICATIONS

International Search Report as mailed on Apr. 28, 2009 for International Patent Application PCT/US2008/088518.

* cited by examiner

*Primary Examiner* — Sanjay Cattungal
(74) *Attorney, Agent, or Firm* — Quarles & Brady LLP

(57) ABSTRACT

A system and method for performing accelerated ultrasound imaging provides significant increases in image acquisition speed using substantially simultaneous transmission of a plurality of ultrasound beams into an object being imaged. The resulting acquired echo signal contributions resulting from the reflection of the simultaneously transmitted beams off different features of the object being imaged are separated by employing a spatial decoding scheme. The spatial decoding scheme characterizes how received signals from features within the object being imaged are measured differently by each of the elements of an ultrasound transducer. The present invention may further include a temporal encoding and decoding scheme, which includes the modulation of a potion of the ultrasound beams transmitted during a portion of ultrasound data acquisition periods, to provide improved separation of the signal components from different features.

15 Claims, 6 Drawing Sheets

SYSTEM AND METHOD FOR ACCELERATED FOCUSED ULTRASOUND IMAGING

CROSS-REFERENCE TO RELATED APPLICATIONS

This application claims the benefit of and incorporates herein by reference U.S. Provisional Application Ser. No. 61/009,683 filed Dec. 31, 2007, and entitled HIGH SPEED ULTRASOUND IMAGING USING MULTIPLE BEAMS.

BACKGROUND OF THE INVENTION

The present invention relates to the field of ultrasound imaging and, more particularly, to a system and method for increasing image acquisition speed.

Ultrasound imaging is a low-cost, safe, and mobile imaging modality that is widely used in clinical radiology. There are a number of modes in which ultrasound can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode).

Ultrasonic transducers for medical applications are constructed from one or more piezoelectric elements sandwiched between a pair of electrodes. Such piezoelectric elements are typically constructed of lead zirconate titanate (PZT), polyvinylidene diflouride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231.

When used for ultrasound imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the echo signal received by each transducer array element.

As indicated above, there are a number of electronic methods for performing a scan using a transducer having an array of separately operable elements. These methods include linear array systems and phased array systems.

A linear array system includes a transducer having a large number of elements disposed in a line. A small group of elements are energized to produce an ultrasonic beam that travels away from the transducer, perpendicular to its surface. The group of energized elements is translated along the length of the transducer during the scan to produce a corresponding series of beams that produce echo signals from a two-dimensional region in the subject. To focus each beam that is produced, the pulsing of the inner elements in each energized group is delayed with respect to the pulsing of the outer elements. The time delays determine the depth of focus which can be changed during scanning. The same delay factors are applied when receiving the echo signals to provide dynamic focusing during the receive mode. A number of such linear array systems are disclosed in U.S. Pat. Nos. 3,881,466; 4,550,606 and 5,097,709.

The second common form of ultrasonic imaging is referred to as "phased array sector scanning", or "PASS". Such a scan is comprised of a series of measurements in which all of the elements of a transducer array are used to transmit a steered ultrasonic beam. The system then switches to receive mode after a short time interval, and the reflected ultrasonic wave is received by all of the transducer elements. Typically, the transmission and reception are steered in the same direction ($\theta$) during each measurement to acquire data from a series of points along a scan line. The receiver is dynamically focused at a succession of ranges (R) along the scan line as the reflected ultrasonic waves are received. A series of measurements are made at successive steering angles ($\theta$) to scan a pie-shaped sector of the subject. The time required to conduct the entire scan is a function of the time required to make each measurement and the number of measurements required to cover the entire region of interest at the desired resolution and signal-to-noise ratio. For example, a total of 128 scan lines may be acquired over a 90° sector, with each scan line being steered in increments of 0.70°. A number of such ultrasonic imaging systems are disclosed in U.S. Pat. Nos. 4,155,258; 4,155,260; 4,154,113; 4,155,259; 4,180,790; 4,470,303; 4,662,223; 4,669,314 and 4,809,184.

The same scanning methods may be used to acquire a three-dimensional image of the subject. The transducer in such case is a two-dimensional array of elements which steer a beam throughout a volume of interest or linearly scan a plurality of adjacent two-dimensional slices.

Ultrasound imaging, which can generate images as fast as the human eye can see them, has a high temporal resolution compared to other imaging modalities. However, image quality is generally sacrificed to achieve these high frame rates and imaging parameters, such as the number of lines per image and the maximum depth, must be adjusted in consequence. Maintaining high frame rates also prevents the practical use of more elaborate imaging techniques, for example, techniques providing improved spatial coverage or multidimensional images. A method able to increase imaging speed would improve the feasibility and utility of such scanning methods. While current frame rates are arguably sufficient in diagnostic ultrasound, faster imaging techniques would be valuable, not necessarily to provide increased frame rates, but to provide more elaborate and improved images while keeping frame rates unchanged.

Synthetic aperture imaging is a fast imaging technique that allows the generation of an image after every transmit event and involves firing a single element of a transducer while receiving signal from all elements. Although fast, synthetic aperture imaging is adversely affected by reduced signal-to-noise ratio (SNR) and increased artifact content. Modifications have been proposed to alleviate these problems, for example, extending acquisition over multiple transmit events, employing several elements to create a focus point that acts as a virtual element with increased power, and firing multiple elements at once (either physical or virtual) using voltage waveforms that are later discriminated during image reconstruction. These waveforms may be designed through techniques such as frequency hopping, frequency division, and the generation of pseudo-random sequences. However, these transmit schemes do not provide adequate image quality when compared to traditional transmit beamforming strategies, especially when imaging objects having the complexity of typical biological systems.

Faster imaging can be performed using receive beamforming, which features abilities to discriminate between echo signal components from different simultaneously-transmitted ultrasound beams and thus allows faster image acquisition. However, the performance of receive beamforming using such techniques is strongly dependent on the precise shape of the transmitted waveforms and, as a result, performance may vary significantly between different imaging situations. In many cases, images produced using this technique may include excessive artifact levels.

It would therefore be desirable to have a system and method for accelerated ultrasound method that provides faster image acquisition without producing significant levels of artifacts. Such a method would allow improvements in image quality and the use of more elaborate scanning techniques, for example, multi-plane imaging, without accompanying reductions in frame rate.

SUMMARY OF THE INVENTION

The present invention overcomes the aforementioned drawbacks by providing a method for producing ultrasound images from ultrasound data acquired by simultaneously transmitting multiple ultrasound beams into an object being imaged and receiving the reflected signal.

In accordance with one aspect of the invention, an accelerated method for producing an image using an ultrasound system is provided. The method includes producing a plurality of ultrasound beams directed at an object being imaged, wherein the plurality of beams are produced substantially simultaneously and wherein the beams are reflected by features within the imaged object to produce echoes. The method also includes measuring the echoes using a transducer having a plurality of elements, wherein the measured echo signals include overlapped components from echoes reflected from multiple spatial locations within the imaged object. The production of multiple ultrasound beams and acquisition of multiple echoes is repeated to scan a region of interest of the object. The method also includes analyzing variations of the measured echo signals across the plurality of transducer elements to separate the overlapped echo signal components and producing an image of the object from the separated signal components.

Various other features of the present invention will be made apparent from the following detailed description and the drawings.

DESCRIPTION OF THE PREFERRED EMBODIMENT

Figure 1:
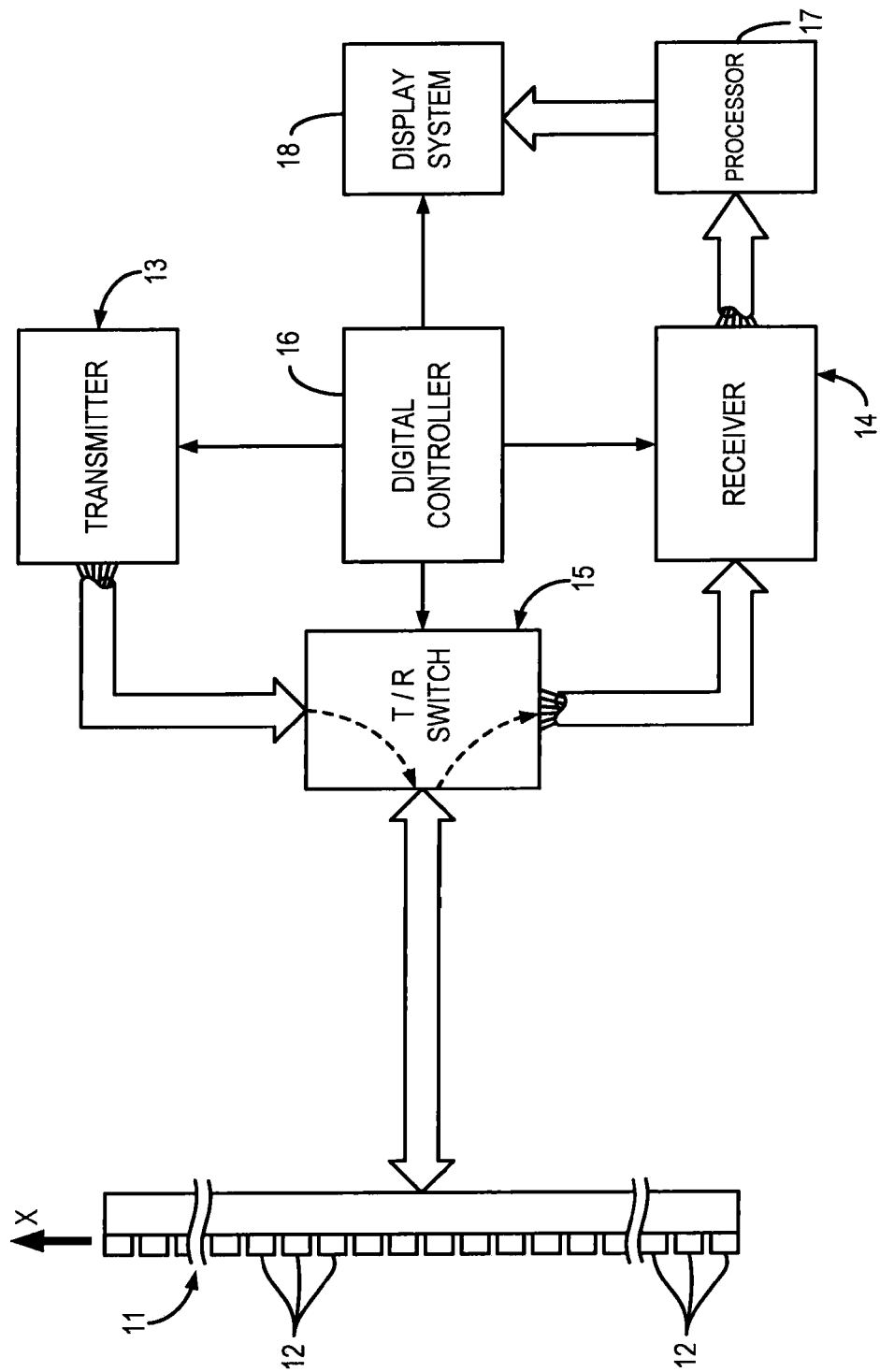
FIG. 1 is a block diagram of an ultrasonic imaging system which employs the present invention.

Referring particularly to FIG. 1, an ultrasonic imaging system includes a transducer array 11 comprised of a plurality of separately driven elements 12 which each produce a burst of ultrasonic energy when energized by a pulse produced by a transmitter 13. The ultrasonic energy reflected back to the transducer array 11 from the subject under study is converted to an electrical signal by each transducer element 12 and applied separately to a receiver 14 through a set of switches 15. The transmitter 13, receiver 14 and the switches 15 are operated under the control of a digital controller 16 responsive to the commands input by the human operator. A complete scan is performed by acquiring a series of echoes in which the switches 15 are set to their transmit position, the transmitter 13 is gated on momentarily to energize each transducer element 12, the switches 15 are then set to their receive position, and the subsequent echo signals produced by each transducer element 12 are applied to the receiver 14. The received data are then reconstructed into an image by the processing unit 17, and sent to a display system 18.

The above-described ultrasound system may be employed to perform a variety of imaging studies, included accelerated ultrasound imaging in accordance with the present invention. In general, the present invention emits multiple ultrasound beams simultaneously in a single 'shot' and employs spatial and temporal decoding schemes to interpret the resulting echo signals. Multiples shots are typically performed to form a given ultrasound image and multiple images may be formed over the course of an examination. It should be noted that the process described below with reference to FIGS. 2 and 5 describes the production of a single image and may be repeated as necessary to allow for the production of a time series of images. This method of the present invention may be referred to as 'Separation of Paths with Element Encoding and Decoding' (SPEED).

Figure 2:
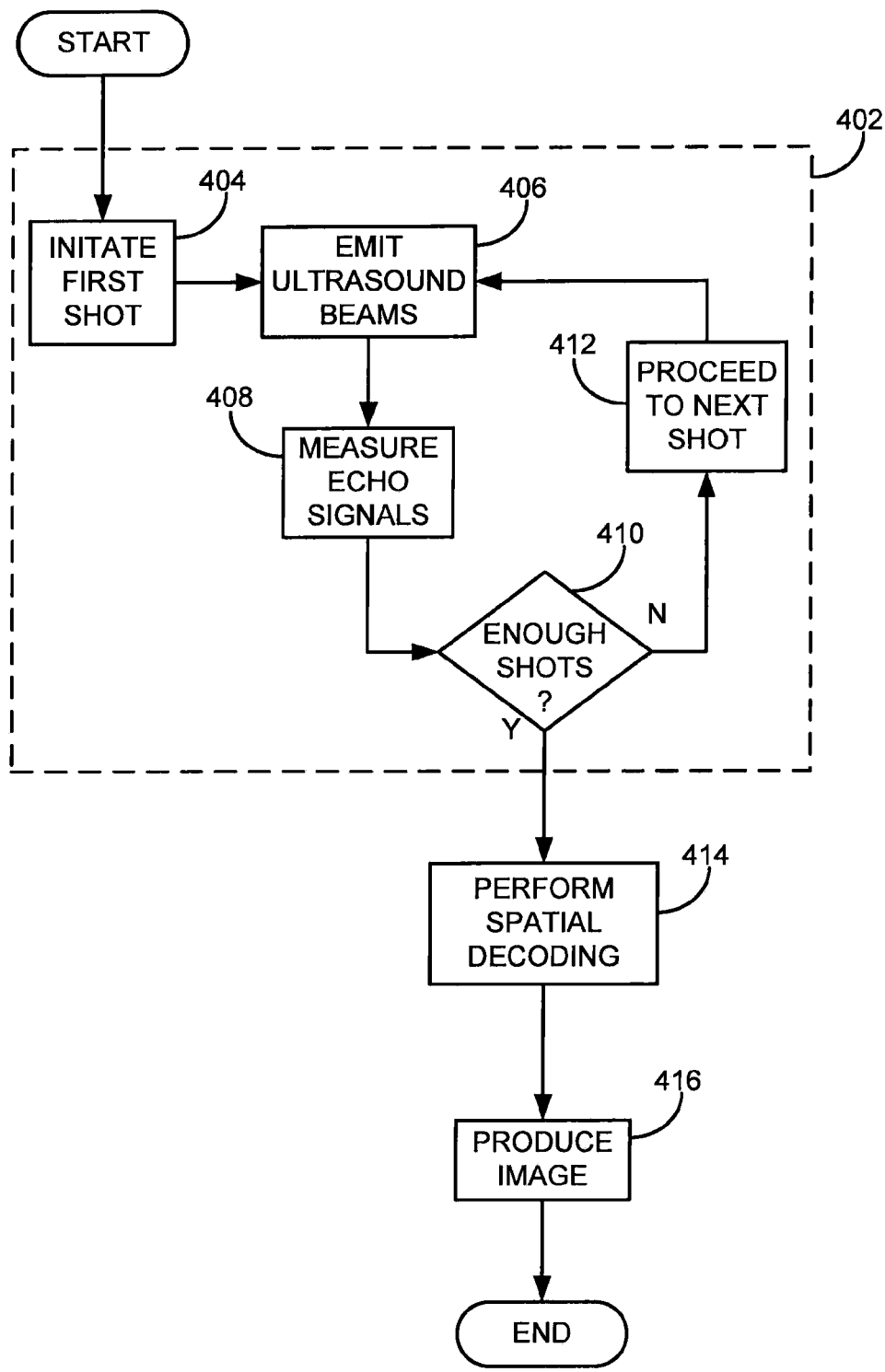
FIG. 2 is a flowchart setting forth the steps for producing an ultrasound image using a spatial encoding and decoding scheme in accordance with the present invention.
Figure 3:
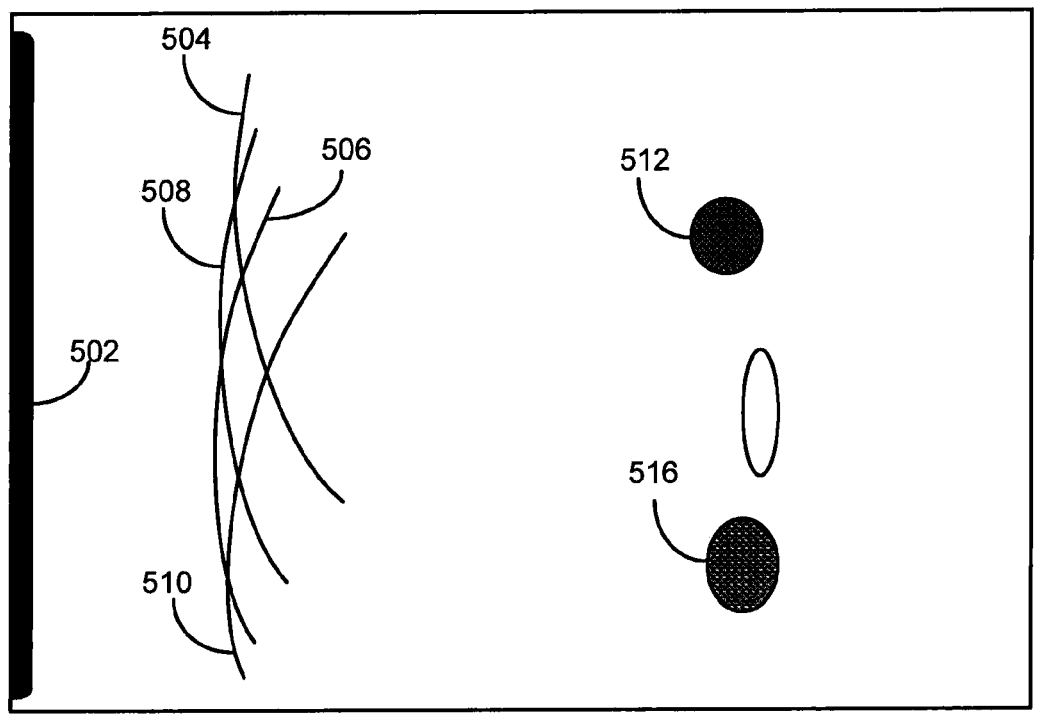
FIG. 3 is an image showing the simultaneous transmission of four ultrasound beams into an object being imaged in accordance with the present invention.

Referring to FIGS. 2 and 3, the present invention begins with the acquisition of ultrasound data, as indicated generally at 402. The acquisition of ultrasound data includes the initialization of a first shot, that is, a period of time during which multiple ultrasound beams are transmitted into an object by an ultrasound transducer. During this first shot, a plurality of ultrasound beams are substantially-simultaneously transmitted from an ultrasound transducer into an object at process block 406. As defined herein, substantially-simultaneous transmission of a plurality of beams includes beams that are spatially close to each other, so the beams effectively combine into a broader, combined beam. Thus, whereas traditional beam transmission schemes generally transmit a single ultrasound beam per given shot, the present invention transmits n beams per shot. For example, a transducer 502 in accordance with the present invention may substantially-simultaneously transmit four beams 504-510 into an object.

At process block 408, echoes, which result from the reflection of the beams off features and boundaries within the object, are received and measured by the elements of the ultrasound transducer to produce ultrasound data. Due to the simultaneous transmission of n ultrasound beams at process block 402, the transducer may simultaneously receive echoes reflected from features at different spatial locations within the object being imaged. Without determining which components of the measured echo signal result from which echo, and thus from which transmitted beam, it is difficult to determine the spatial location of the features being imaged. Images produced from this ultrasound data without further processing will generally be corrupted by artifacts. For example, the transducer 502 may simultaneously receive echoes resulting from the reflection of beam 504 off object 512 and the reflection of beam 510 off object 516. Without separating the measured echo signal component resulting from the reflection of beam 504 from the echo signal component resulting from the reflection of beam 510, the spatial locations of objects 512 and 516 would be difficult to discern. Interpreting the ultrasound data and discriminate between echo signal contributions from different spatial locations is referred to as 'spatial decoding' and will be discussed later.

Referring still to FIGS. 2 and 3, at decision block 410 it is decided if enough shots have been performed to acquire an amount of ultrasound data sufficient to form an image. Typically each shot acquires information describing only a portion of a region-of-interest (ROI) being imaged and multiple shots are therefore performed to produce a given image. If more ultrasound data is required, the present invention proceeds to the next shot at process block 412 and beam transmission at process block 406 and echo measuring at process block 408 are repeatedly performed in the above-described manner until, at decision block 410, it is decided that a sufficient number of shots have been performed and a sufficient amount of ultrasound data has been acquired. While a traditional beam transmission scheme would generally include $N_l$ shots to acquire the $N_l$ lines that form a given image, the present invention may employ only $(N_l/n)$ shots to form the same image. For example, the transducer 502 transmitting four beams 504 per shot would allow the formation of an image using $(N_l/4)$ shots, permitting an acceleration factor of four over traditional beam transmission schemes.

Referring again to FIG. 2, a spatial decoding process is performed at process block 414 to separate, or 'decode', simultaneously received echo signal components from different features, that is, different spatial locations, within the imaged object. Because the features are at different spatial locations within the imaged object, they distribute their reflected echoes in different ways over the multiple elements of a multi-receiver transducer, thus leading to intensity and phase signatures over the transducer elements. This causes the overlapped echoes to be 'felt' differently by each of the many transducer elements and allows decoding to be performed to separate the overlapping signal components.

The way different signals are felt by the many elements of a transducer is independent of the object being imaged and may be characterized by a spatial encoding matrix E, which describes the forward transform, from object to measured signal, that is performed by an ultrasound imaging system. This relationship may be modeled by the following equation:

$$s = Eo + \xi \qquad \text{Eqn. 1}$$

where s is a vector containing all of the signal points measured by the transducer in a single shot, o is a vector containing one entry for each object voxel probed in a given shot, E is the spatial encoding matrix relating the object voxels to the measured signal, and $\xi$ represents random digitized noise.

It is contemplated that if $N_t$ time points are sampled by each of $N_e$ transducers, then the vector s includes $N_t$ modules pasted one after another, wherein each module includes the data measured by all $N_e$ elements at a given time point. With this structure, the vector s would include $(N_t \times N_e)$ elements. It is further contemplated that the vector o includes $(n \times N_{ax})$ elements for an acquisition with $N_{ax}$ image voxels in the axial direction and n beams per shot. This vector o may be structured to include n modules pasted one after another, wherein each image module includes $N_{ax}$ voxels along a given beam.

Figure 4:
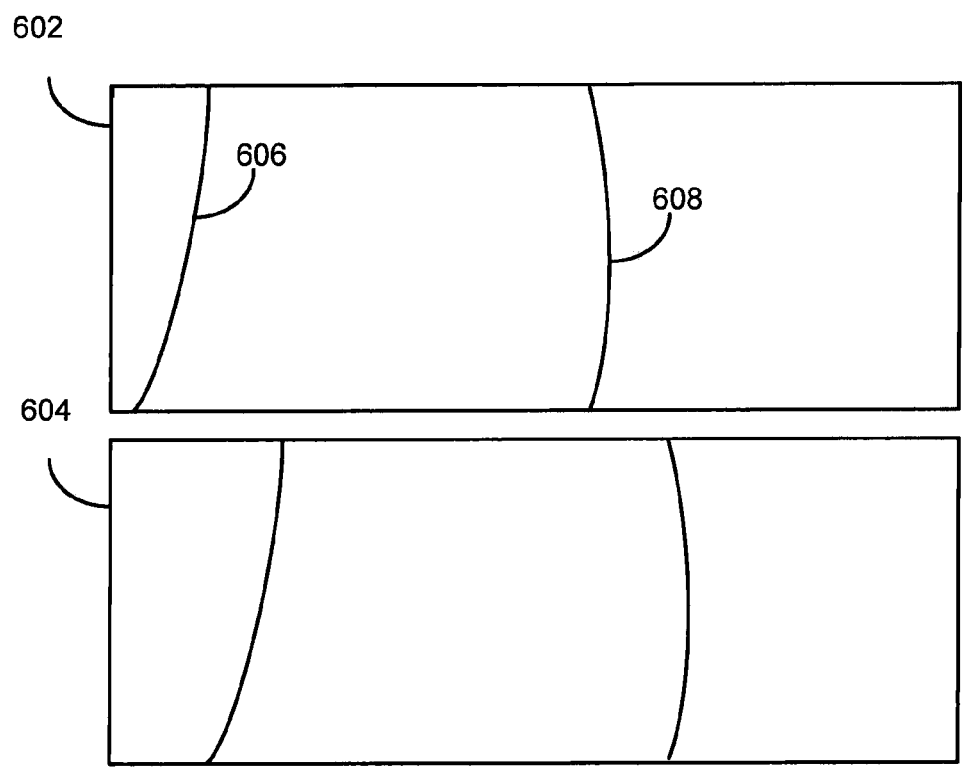
FIG. 4 is a schematic representing two entries of an encoding matrix in accordance with the present invention.

Referring particularly to FIG. 4, the encoding matrix E may be an elongated, vertical matrix, which includes $(N_t \times N_e)$ rows and $(n \times N_{ax})$ columns, and is structured to have $N_t$ modules pasted one after another, wherein each module is $N_e$-by-$(n \times N_{ax})$ in size. For example, E may include a module representing a first shot 602 and a module representing a later shot 604. In this exemplary acquisition n=2 and the modules include signals resulting from beam number one and beam number $(N_l/2)$. Beam number one may remain close to the first transducer element as it propagates and, as a result, signals measured by this element at a given time come from deeper within the object than signals measured by other elements. This relationship leads to the shape 606. Alternately, beam number $(N_l/2)$ may propagate nearly perpendicular to the transducer face and elements in the middle of the transducer array receive signals from deeper within the object, leading to the curved shape 608. The beams propagate deeper into the object and later modules, for example, module 604, contain information corresponding to deeper locations and resemble versions of the first module 602 that are shifted towards higher axial distances. The modules may also include signal intensity variations due to geometric and attenuation effects.

As described above, E of Eqn. 1 depends on the geometry of the transducer and other imaging parameters such as the number of lines, the angular range covered by these lines, and the imaging depth. Inconsistencies between the modeled E and the encoding performed by the actual system, as well as poor conditioning of E and system noise, may reduce image quality and increase artifact levels. It is therefore contemplated that imaging performance may be improved by including additional factors, along with geometrical and attenuation effects, when modeling E. Examples of these additional factors include the actual voltage waveform used when firing the transducer elements, the frequency response of the elements, and any prior knowledge about spatial variations in the speed of sound.

Referring again to FIG. 2, the spatial encoding matrix E may be inverted to produce a decoding matrix D, which can be employed in the following, inverted form of Eqn. 1:

$$\hat{o} = Ds \quad \text{Eqn. 2;}$$

where ô is an estimate of scatter strength at spatial locations found along insonified beams. Eqn. 2 may be solved for ô to produce spatially decoded image data that is used to produce an image at process block 416. The above-described process may therefore be performed repeatedly to produce a plurality of images or 'frames' that may be used to produce the time series of images commonly used in ultrasound examinations.

Figure 5:
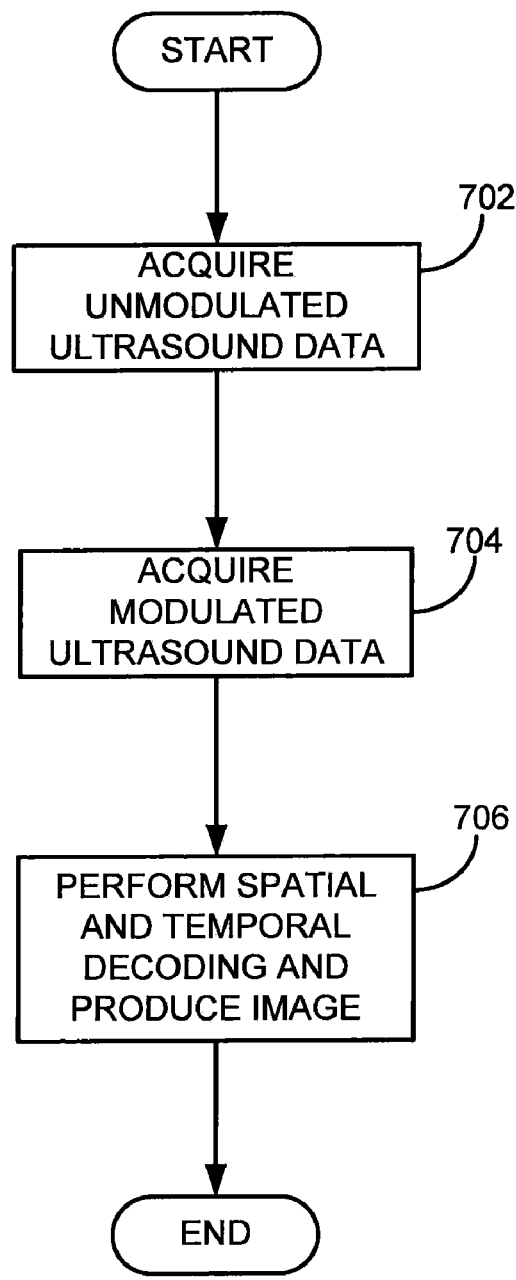
FIG. 5 is a flowchart setting forth the steps for producing an ultrasound image using temporal and spatial encoding and decoding schemes in accordance with the present invention.
Figure 6:
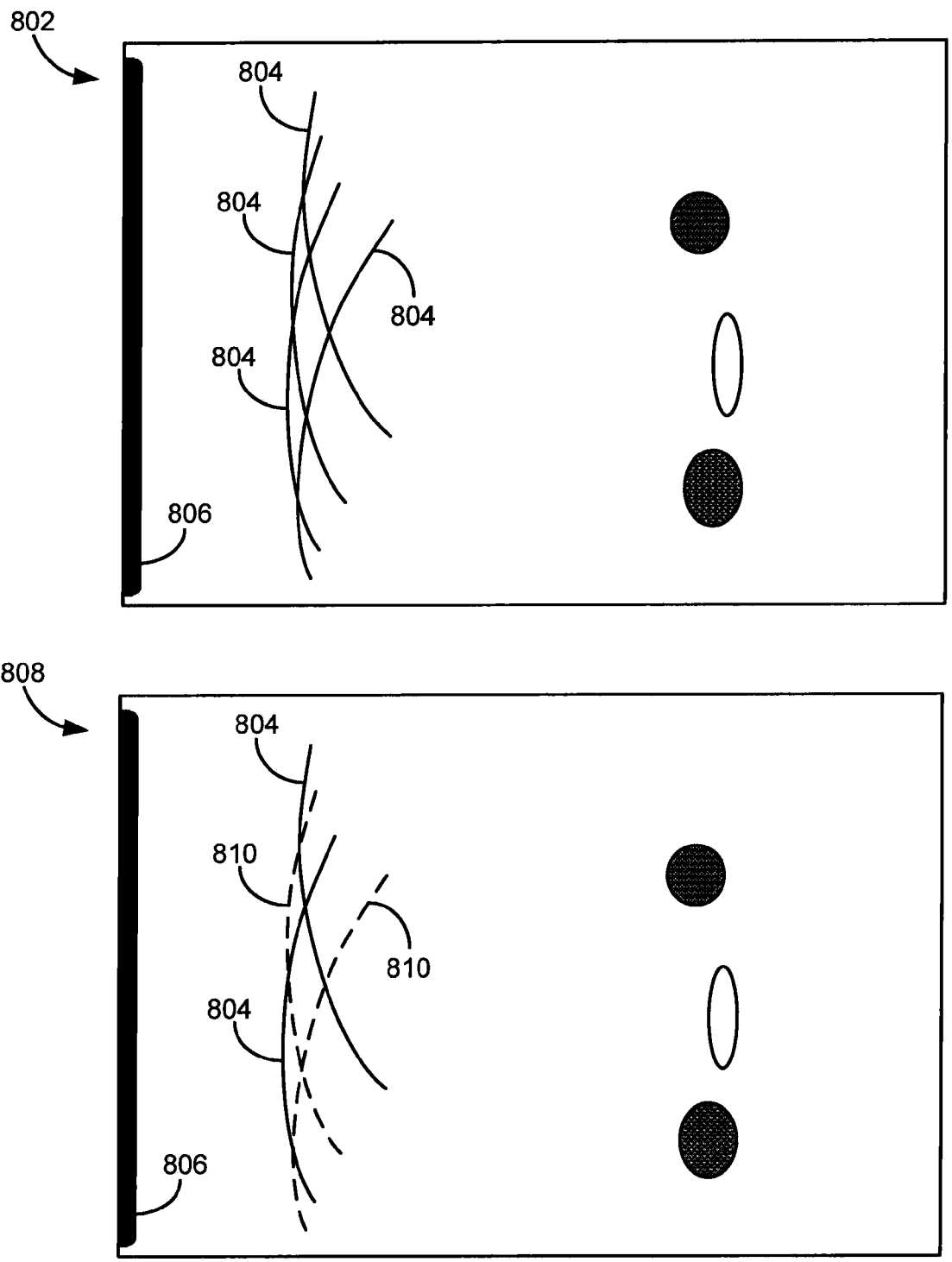
FIG. 6 is a series of images showing the simultaneous transmission of a plurality of ultrasound beams using temporal encoding in accordance with the present invention.

Referring now to FIGS. 5 and 6, the present invention may employ a temporal encoding and decoding scheme to further discriminate between the echo signal contributions from each of the n substantially-simultaneously transmitted beams. The production of an image using a temporal encoding and decoding scheme begins at process block 702 with the acquisition of unmodulated ultrasound data using a process similar to that described with respect to FIG. 2 and, more particularly, described with reference to sub-process 402. Following the acquisition of unmodulated ultrasound data, modulated ultrasound data is acquired at process block 704. The acquisition of modulated ultrasound data employs a scan that is generally similar to the acquisition of unmodulated data at process block 702, but includes the modulation of a portion of the beams transmitted during each shot. Beam modulation may be performed by reversing the phase of a given beam. For example, a shot for the acquisition of unmodulated ultrasound data 802 may include four uninverted beams 804 transmitted from a transducer 806, while a shot for the acquisition of modulated ultrasound data 808 may include alternating uninverted beams 804 and inverted beams 810. In an overall ultrasound scan that includes the repeated production of images for the construction of a time series of image frames, it is contemplated that temporal encoding may be employed to invert every second beam of every ultrasound data acquisition process. The alternating acquisition of modulated ultrasound data is referred to as 'temporal encoding' and causes signals in modulated ultrasound images to become inverted compared to signals at equivalent locations in unmodulated ultrasound images. Analyzing the differences between modulated and unmodulated ultrasound images allows the identification of regions where beams overlap, further allowing the identification and correction of aliasing artifacts. The process by which temporal encoding is accounted for and used to improve image quality is referred to as 'temporal decoding'.

Referring to FIG. 5, at process block 706, a temporal and spatial decoding and reconstruction process is performed on modulated and unmodulated ultrasound data, which is now designated $D_m(s, r, t)$, to produce a time series of images I(x, y, z, t). Decoding may be described by the following equation:

$$I(x,y,z,t) = C\{F_{-DC,Ny}\{O_n\{D_m(s,r,t)\}\} + O_l\{F_0\{D_m(s,r,t)\}\}\} \quad \text{Eqn. 3}$$

where C{ . . . } is an operator that performs envelope detection and Cartesian gridding; $O_n\{\ldots\}$ and $O_l\{\ldots\}$ are spatial decoding operators that employ the decoding matrix D in the manner described with reference to Eqn. 2 to separate n overlapped beams; l is the number of overlapped beams sharing the same temporal modulation scheme and is equal to either floor (n/2) or ceil (n/2), depending on the particular beam being processed; $F_{-Dc, Ny}$ is an operator that removes regions around the DC and Nyquist temporal frequencies; and $F_0$ is an operator that selects only a frequency band around either the Nyquist temporal frequency or the DC temporal frequency, depending on whether the particular beam being processed is Nyquist modulated or not, respectively.

Figure 7:
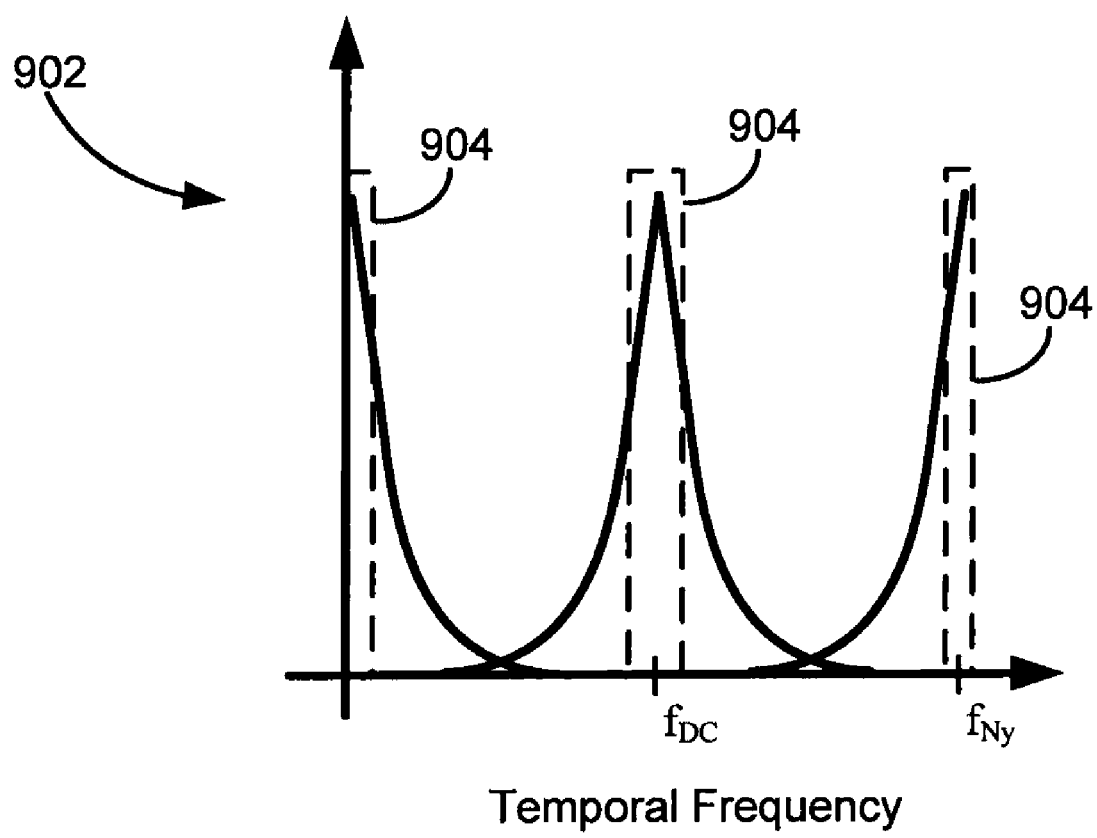
FIG. 7 is an image showing the temporal frequency domain and the modulation and shifting of overlapping echo signal components in accordance with the present invention.

Referring now to FIG. 7, failure to separate the echo signal contributions of n overlapping beams with the spatial operator $O_n\{\ldots\}$ may produce image artifacts. Temporal encoding, when forcing some beams to reverse phase in alternating frames, imposes a Nyquist modulation on some of the beams and helps discriminate signals associated with modulated beam from signals associated with unmodulated beams. This idea can be understood by considering a representation of the temporal frequency domain 902. In this case, overlapped signal components are modulated and shifted towards higher frequencies, creating a region 904 where aliasing problems are less serious. In this region with reduced aliasing 904, the operator $O_l$, where l≈(n/2), may be employed instead of $O_n\{\ldots\}$. Placing the better-behaved regions near the temporal DC frequency ($f_{DC}$) and Nyquist frequency ($f_{Ny}$) where most of the signal energy is expected simplifies the task of separating overlapping signal components and produces reduced levels of artifacts. A reduction in temporal resolution is incurred when employing temporal encoding and decoding due to the loss of a narrow frequency band around the Nyquist frequency. However, the reduction in temporal resolution is small and is of limited practical consequence. For example, using filters with a half-width-half-maxima equal to ten-percent of bandwidth and with a time τ to acquire one time frame, temporal resolution is only reduced from a value of τ to a value of (1.1×τ).

It should be noted that E, and thus its inverse D, do not depend on the imaged object, allowing the present invention to image complex objects without additional difficulty and thereby overcoming a serious shortcoming of previous methods for performance faster ultrasound imaging. This independence also allows the decoding matrix D to be calculated using either numerical solving techniques or direct matrix inversion. Using numerical techniques the decoding matrix D may, for example, be calculated using the regularized least squares approach:

$$D = (E^H \psi^{-1} E + \lambda^2 L)^{-1} E^H \psi^{-1} \quad \text{Eqn. 4;}$$

where $\lambda^2 L$ is a damped least squares regularization term and $\psi^{-1}$ can be used for preconditioning purposes. $\psi$ and L are often identity matrices, but they may additionally incorporate prior knowledge regarding noise correlation and/or object signal. Regularization suppresses noise amplification that may occur when the system defined by E is poorly conditioned, while preconditioning can manipulate the spectrum of E to reduce the system condition number and/or produce a more computationally tractable problem. For example, when $\psi^{-1}$ is square and complex conjugate symmetric, then $E^H \psi^{-1} E$ is also square and complex conjugate symmetric.

Direct inversion of E may also be performed to calculate D. Direct inversion is a computationally expensive process that would be prohibitively slow to perform during each of the many decoding and reconstruction processes that are typically included in an ultrasound examination. However, E is not dependent on the object being imaged and direct inversion can therefore be performed in advance of an ultrasound examination, allowing a repository of decoding matrices D associated with common imaging parameters for a given transducer to be precalculated and saved. Relevant decoding matrices D could then be loaded for a given scan and employed to decode and reconstruct real-time data with comparable speed to traditional digital receive beamforming reconstruction.

The method of the present invention may be generalized by considering transmit events that reach all object locations. If ultrasound energy is assumed only to travel along well-defined beams, then the number of insonified locations per transmit event is limited to only $(n \times N_{ax})$ voxels, allowing the reconstruction of all $(N_l \times N_{ax})$ voxels to be broken into $(N_l/n)$ independent and smaller problems. Generalizing the method would lift the assumption that ultrasound energy is confined to narrow beams, but may also lead to larger E matrices with poorer conditioning and longer processing times. Moreover, additional speed and performance may be provided by combining the present invention with transmit-based encoding schemes such as synthetic aperture imaging.

Instead of several separate beams as shown in FIG. 6, one could use a single, broader excitation beam instead, in a way consistent with the prior art named 'explososcan'. While the use of one broad excitation beam would appear to be mostly incompatible with the temporal scheme proposed here, it would be quite compatible with the spatial scheme. The solution proposed in Eqn. 4 would then prove significantly more accurate than the receive-beamforming reconstruction used as part of explososcan.

As previously mentioned, ultrasound images produced in accordance with the present invention, such as the ultrasound images produced at process block 416 and 706 of FIGS. 2 and 5 respectively, may be used to construct a time series of images. In a typical ultrasound examination a time series of images is acquired and displayed at a rate of approximately twenty frames-per-second (FPS). Because it significantly increases image acquisition speed, the present invention may be employed to increase the display frame rate. However, frame rates provided by traditional methods are generally considered adequate and it is therefore contemplated that the present invention may instead be used to improve the quality of image frames within a time series without causing any decreases in frame rate. This may generally be achieved by combining a plurality of the ultrasound images produced at process blocks 416 and 706 into a single image frame.

For example, the present invention may be employed to increase spatial resolution, allowing the number of lines per image $N_l$ to be increased while keeping frame rates unaffected. The present invention may be also employed to enable multifocus imaging. Lateral resolution, which tends to be superior near the focus and degrades away from the focus, can be improved by acquiring n images with different focal lengths and interleaving these images to produce a composite image. Similarly, it is also contemplated that the present invention may provide 3D coverage without incurring any frame rate penalties. With an acceleration factor of n, 3D coverage may be achieved using a 2D phased-array transducer by acquiring and combining ultrasound data from n different planes. 3D coverage may be improved by determining how to best combine individual beams into groups of n, and acceleration factors in 3D imaging could be improved as compared to 2D imaging through applying acceleration along two directions rather than only one.

The sharpness of ultrasound images may be improved using the present invention. When imaging, spatial locations $(r, \theta)$ are encoded through a unique function in the RF signal into a space of dimension $N_e$-by-$N_r$. A correlation map can be generated for the encoding functions corresponding to all beams at a given value of r. The off-diagonal terms of the correlation map correspond to cross-correlation between closely related locations and lead to blurring. Image sharpness can be improved by employing to present invention to resolve these correlations and reduce blurring.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image using an ultrasound system, the steps comprising:
   a) acquiring ultrasound data by:
      i) producing a plurality of ultrasound beams during a given shot directed at an object being imaged, wherein the beams are reflected by features within the imaged object to produce echoes;
      ii) measuring the echoes using a transducer having a plurality of elements, wherein the measured echo signals include overlapped components from echoes reflected from multiple spatial locations within the imaged object;
      iii) repeating steps i) and ii) to scan a region of interest of the object;
   b) analyzing variations of the measured echo signals across the plurality of transducer elements to separate the overlapped echo signal components by employing a spatial decoding matrix that relates the spatial locations from which echoes were reflected to the variations of the measured echo signal between each of the transducer elements; and
   c) producing an image of the object from the separated signal components.

2. The method as recited in claim 1 wherein the spatial decoding matrix is the inverse of a spatial encoding matrix, which is dependent on the geometry of the transducer and on imaging parameters.

3. The method as recited in claim 2 wherein the imaging parameters include geometric and attenuation effects, a number of lines in an image, an angle range covered by the lines, and imaging depth.

4. The method as recited in claim 3 wherein the imaging parameters further include timing effects due to the geometry of the transducer and imaged field-of-view, information describing a voltage waveform used to produce the plurality of ultrasound beams, and a frequency response of the transducer elements.

5. The method as recited in claim 3 wherein the spatial decoding matrix is calculated from the spatial encoding matrix by direct inversion and wherein the decoding matrix for a given transducer is precalculated for a plurality of imaging parameters and stored by the ultrasound system.

6. The method as recited in claim 3 wherein the spatial decoding matrix is calculated from the spatial encoding matrix using a numeral calculation technique.

7. The method as recited in claim 1 wherein the plurality of beams are produced substantially simultaneously.

8. The method as recited in claim 1 further including:
   a) iv) producing an additional plurality of ultrasound beams during another given shot directed at the object being imaged, wherein at least one of the additional beams is modulated, and wherein the additional beams are reflected by the features within the imaged object to produce additional echoes;
   a) v) measuring the additional echoes using the transducer having a plurality of elements, wherein the additional measured echo signals include overlapped components from echoes reflected from the multiple spatial locations within the imaged object; a) vi) repeating steps iv) and v); and b) i) analyzing the measured echo signals and the additional measured echo signals to separate overlapped echo signal components from different spatial locations.

9. The method as recited in claim 8 wherein step a) iv) includes modulating every second additional beam and wherein modulated beams include a reversed phase.

10. The method as recited in claim 9 wherein step b) includes:
   i) employing a first spatial decoding operator to separate the overlapped echo signal components;
   ii) removing signals in regions near a temporal DC frequency and temporal Nyquist frequency from the signal produced in step b) i);
   iii) removing signals outside the regions near at least one of the temporal DC frequency and temporal Nyquist frequency from the overlapped echo signal components; and
   iv) employing a second spatial decoding operator to spatially decode the overlapped echo signal components produced in step b iii).

11. The method as recited in claim 10 wherein step c) includes employing an envelope detection and Cartesian gridding operator to produce the image of an object from the separated signals produced in step b) ii) and b) iv).

12. The method as recited in claim 11 wherein the first and second spatial decoding operators employ a spatial decoding matrix that is the inverse of a spatial encoding matrix, which is dependent on the geometry of the transducer and imaging parameters.

13. The method as recited in claim 10 wherein steps a) to c) are repeated to produce a plurality of images of the object.

14. The method as recited in claim 13 wherein the plurality of images of the object are processed and combined to produce improved image frames.

15. The method as recited in claim 14 wherein the improved image frames include at least one of an improved spatial resolution, an improved sharpness, an increased focal range, and 3D coverage.

* * * * *